United States Patent [19]

Terrill

[11] 4,091,091
[45] May 23, 1978

[54] STABILIZED NITROGLYCERIN TABLETS
[75] Inventor: Paul Meredith Terrill, Danville, Ind.
[73] Assignee: Eli Lilly and Company, Indianapolis, Ind.
[21] Appl. No.: 414,019
[22] Filed: Nov. 8, 1973
[51] Int. Cl.$^2$ .................. A61K 9/20; A61K 31/21; A61K 31/79
[52] U.S. Cl. ........................................ 424/80; 424/298
[58] Field of Search .................. 424/80, 298; 260/467

[56] References Cited

U.S. PATENT DOCUMENTS

| | | | |
|---|---|---|---|
| 3,028,307 | 4/1962 | Ninger | 424/298 |
| 3,102,845 | 9/1963 | Fennell | 424/80 |
| 3,344,029 | 9/1967 | Berger | 424/298 |
| 3,428,728 | 2/1969 | Lowey | 424/298 |
| 3,789,119 | 1/1974 | Fusari et al. | 424/78 |
| 3,873,727 | 3/1975 | Fusari et al. | 424/366 |

FOREIGN PATENT DOCUMENTS 1,090,184  11/1967  United Kingdom.

OTHER PUBLICATIONS

Prescott et al., Texas J. Pharm. 4(3): 300–8 Summer 1963, "Pharmaceutical Dispersed Systems Featuring Plasdone".
GAF Brochure TA-67 FO-50, "Plasdone for Oral Pharmaceuticals", 7 pp., May, 1961.
Fung et al., J. Pharm. Sci. 63 (11):1810–1811, Nov. 1974, "Development of a Stable Sublingual Nitroglycerin Tablet I: Interaction of Nitroglycerin With Selected Macromolecules".
Hargrove Tile & Till 59(4): 65 Dec. 1973, "Nitroglycerin—Facts Today".

*Primary Examiner*—Shep K. Rose
*Attorney, Agent, or Firm*—Ralph W. Ernsberger; Everet F. Smith

[57] ABSTRACT

A pharmaceutical preparation is described which comprises nitroglycerin tablets stabilized against the migration of the active agent from tablet to tablet when such tablets are in contact with each other.

A method is provided for stabilizing such nitroglycerin tablets.

9 Claims, No Drawings

4,091,091

STABILIZED NITROGLYCERIN TABLETS

BACKGROUND OF THE INVENTION

1. Field of Invention

This invention relates to pharmaceutical tablets. Specifically, this invention provides a nitroglycerin tablet for oral administration which is stabilized to maintain a uniform content of nitroglycerin in the tablets when such tablets are in contact with each other.

2. Description of the Prior Art

Glyceryl trinitrate, hereinafter referred to as nitroglycerin, has been employed in the alleviation of the distress of angina pectoris for many decades. Angina pectoris is a clinical condition which is the result of constrictions developing in the arteries of the heart. When these constrictions develop, angina pectoris patients experience severe pains in the chest from time to time. Nitroglycerin is employed to dilate the cardiac arteries with the subsequent relief of the pain.

Patients afflicted with angina pectoris require an almost immediate response to the drug, not only for the relief of the excruciating pain that is experienced in such attacks, but also for the remission of the fright which often accompanies the pain due to the relationship with the heart. Consequently, nitroglycerin has been formulated in preparations which can be taken orally by the angina pectoris sufferer and provide relief within a very few minutes. Conventionally, nitroglycerin has been formed into what are called molded tablets which contain soluble ingredients and can be placed under the tongue to achieve a rapid onset of the action of the drug.

Nitroglycerin has a vapor pressure of about 0.00026 m.m. at 20° C. Moreover, nitroglycerin is a violent explosive which must be handled with great care. It was found a long time ago that a safe and effective preparation containing nitroglycerin could be prepared by triturating 1 part of nitroglycerin and 9 parts of beta-lactose. This 10 percent nitroglycerin trituration can then be further diluted with other agents for the preparation of tablets of nitroglycerin containing varying amounts of the drug. Not all angina pectoris sufferers require the same amount of nitroglycerin for the relief of the symptoms associated with such a condition. Consequently, it has been conventional in the pharmaceutical art to supply the trade with at least four different strengths of nitroglycerin tablets. These are: 1/400, 1/200, 1/150, and 1/100 grains of nitroglycerin per tablet.

Recently, it has been found that tablets of nitroglycerin, when packaged in a container wherein bulk tablets are in contact with one another, do not maintain a uniform potency with age. However, this lack of uniformity of potency does not indicate a loss of the nitroglycerin per se but rather the migration of the nitroglycerin from one tablet to another when such tablets are in random orientation in contact with each other. It has been found that over a period of a year as much as 20 percent or more of the nitroglycerin in a tablet could be lost by that tablet through contact with another tablet of like composition. Conversely, another tablet could gain as much or more potency through the absorption of migrating nitroglycerin. The exact cause of this phenomenon is not known. However, it is suspected that capillarity may play some part in producing this untoward and totally unacceptable condition.

Accordingly, it is an object of this invention to provide pharmaceutical tablets containing nitroglycerin which are stabilized against the migration of the active agent from tablet to tablet when such tablets are in contact with each other in conventional pharmaceutical packaging material.

Another object of this invention is to provide pharmaceutical tablets containing nitroglycerin which are stabilized against the migration of the active agent from tablet to tablet when such tablets are in contact with each other and which can be orally administered for dissolution under a patient's tongue without impairing the rapid solubility of the tablet.

Still another object of the instant invention is to provide pharmaceutical tablets of nitroglycerin which are stabilized against the migration of the active agent from tablet to tablet when such tablets are in contact with each other and which can be administered orally under the tongue with no change in the taste or mouth feel of the tablet.

Another object of the present invention is to provide a method for the preparation of pharmaceutical tablets of nitroglycerin which are stabilized against the migration of the active agent from tablet to tablet when such tablets are in contact with each other.

SUMMARY

It has now been discovered that pharmaceutical tablets containing nitroglycerin comprised of: nitroglycerin, polyvinylpyrrolidone, and an excipient or combination of excipients selected from the group consisting of lactose, beta-lactose, milk sugar, fructose, maltose, sucrose, mannitol and sorbitol are stabilized against the migration of the active agent from tablet to tablet when such tablets are in contact with each other and such tablets containing nitroglycerin dissolve promptly when placed under the tongue and are of the same taste and mouth feel as those nitroglycerin tablets which have been available to the angina pectoris patient heretofore.

It has further been discovered that such pharmaceutical tablets can be prepared by dispersing the polyvinylpyrrolidone in an alcohol-water solution and admixing such a dispersion with a nitroglycerin trituration comprised of nitroglycerin and an excipient or combination of excipients selected from the group consisting of lactose, beta-lactose, milk sugar, fructose, maltose, sucrose, mannitol and sorbitol, prior to forming the tablet.

DESCRIPTION OF THE PREFERRED EMBODIMENTS

One aspect of this invention relates to novel pharmaceutical tablets containing nitroglycerin which comprise nitroglycerin, polyvinylpyrrolidone and an excipient or combination of excipients selected from the group consisting of lactose, beta-lactose, milk sugar, fructose, maltose, sucrose, mannitol and sorbitol.

The novel pharmaceutical tablets of this invention can contain from about 0.5 percent to about 5 percent of nitroglycerin. Because there are a number of different strengths of nitroglycerin tablets provided to fill the need for varying doses of the active agent by patients suffering in different degrees from angina pectoris, the nitroglycerin concentration is of relatively little importance.

On the other hand, the concentration of the polyvinylpyrrolidone is of critical importance. It was found that the concentration of polyvinylpyrrolidone related to the final dry weight of the tablet was most useful in the range of from 0.5 percent to about 2 percent, preferably, about 1 percent. It is essential that sufficient polyvinylpyrrolidone be incorporated with the nitroglycerin and the excipient employed in the tablet to impede the development of avenues of capillarity. At the same time it is important that the amount of polyvinylpyrrolidone be maintained at the lowest quantity consistent with the impeding of the opportunities for capillarity in order that the dissolution time of the tablet not be increased beyond that which is consistent with the need for rapid solubility to assure the rapid onset of action by the nitroglycerin when the tablet is taken by the patient. Consequently, a polyvinylpyrrolidone concentration of about 1 percent of the final dry weight of the tablet was determined to be a preferred amount to be employed.

For the safety reasons expressed hereinabove the nitroglycerin is diluted with beta-lactose, or the like, to a concentration that does not exceed 10 percent prior to the undertaking of pharmaceutical compounding and processing. In practice it is desirable that the nitroglycerin concentration in a pharmaceutical tablet should be even less that 10 percent. This is so because it is good pharmaceutical practice to make a tablet sufficiently large that it can be handled easily by a patient, and this, coupled with the relatively small amounts of nitroglycerin administered in each dose, makes it necessary that additional excipients be employed in the preparation of such tablets. Another desirable feature which is important in the preparation of the nitroglycerin tablets is the utilization of readily soluble materials which are chemically compatible with the active agent. Excipients such as the beta-lactose preferably employed in the dilution of the nitroglycerin to the 10 percent concentration can be used as an excipient, but as a general policy due to the higher cost of this purified fraction of milk sugar, it is more reasonable to utilize as an added excipient such soluble materials as lactose, milk sugar, fructose, maltose, sucrose, mannitol and sorbitol. All of these agents are saccharides. They are pharmacologically inert and non-toxic and, moreover, they are materials with which nitroglycerin is compatible. Of the excipients named above, those which are derived from milk are the preferred materials. This is so because the lactoses are generally not as hygroscopic as the other sugars.

Nitroglycerin tablets prepared only from nitroglycerin and an excipient or combination of excipients such as the lactoses have been shown to be subject to a significant degree of migration of the nitroglycerin from tablet to tablet when such tablets are packaged in contact with each other. When nitroglycerin tablets designed to contain 0.65 mg. of active agent were individually analyzed to determine the coefficient of variation in the nitroglycerin content between the tablets, it was found in assaying thirty tablets from each of 17 lots that the coefficient of variation was 3.93 percent after packing the tablets into containers to be delivered to the shipping room. On the other hand nitroglycerin tablets of the same potency containing 1 percent polyvinylpyrrolidone upon analysis of thirty individual tablets from twenty lots showed a coefficient of variation of 2.82 percent immediately after preparation, and only 2.87 percent after packaging.

Moreover, the average weight variation (not to be confused with coefficient of variation percentage) for the tablets made with the formula containing polyvinylpyrrolidone was 5.03 percent. The average weight variation for the tablets containing no polyvinylpyrrolidone was 5.60 percent.

Individual analyses of 30 tablets from each of twenty lots of nitroglycerin tablets designed to contain 0.43 mg. of active agent and containing no polyvinylpyrrolidone showed a coefficient of variation immediately after production of 5.16 percent and of 8.12 percent after packaging. Similar strength tablets containing 1 percent polyvinylpyrrolidone exhibited a coefficient of variation for 30 tablets from each of 20 lots of 3.01 percent immediately after molding and of 3.05 percent after packaging for the market.

In each case the packaging was in bottles containing 100 tablets randomly oriented, and there was a week or more between the assays after molding and after packaging.

The data discussed above clearly demonstrate the benefits in stabilizing tablets of nitroglycerin by adding polyvinylpyrrolidone to the composition.

The coefficient of variation percentage was computed by determining the standard deviation for the differences in the nitroglycerin content from tablet to tablet, dividing the standard deviation by the mean of the tablets analyzed, and multiplying this result by 100.

Another aspect of this invention relates to the process for preparing the novel stabilized nitroglycerin tablets having the composition described hereinbefore. The process by which the stabilized nitroglycerin tablets are prepared comprises the steps of: (a) commingling nitroglycerin with micronized beta-lactose to produce a nitroglycerin trituration in which the content of the active agent is about 10 percent; (b) adding and mixing an excipient or combination of excipients selected from the group described hereinbefore to produce a nitroglycerin trituration having approximately the nitroglycerin concentration desired in the final dry tablet; (c) dispersing an amount of polyvinylpyrrolidone approximately equal to from about 0.5 percent to about 2 percent of the final dry tablet weight in an approximately 2:1 alcohol-water solution in a ratio of approximately 1:10; (d) admixing the polyvinylpyrrolidone dispersion of (c) with the nitroglycerin trituration of (b); and (e) forming a nitroglycerin tablet having the desired active ingredient concentration from the admixture of (d).

In a preferred process, the amount of polyvinylpyrrolidone employed will approximate 1 percent of the final dry weight of the nitroglycerin tablet. The alcohol-water solution into which the polyvinylpyrrolidone is dispersed is preferably comprised of about 2 parts alcohol to 1 part water. In practice it is conventional to divide the total quantity of the nitroglycerin trituration into two or more sections and the polyvinylpyrrolidone dispersion into an equal number of sections. Just prior to forming the nitroglycerin tablets, one section of each of the two materials is brought together. By following this procedure it is possible to maintain the optimum amount of fluid in the tableting material through the forming operation making it possible to mold the tablets into objects of more uniform size and weight.

It will be recognized by those skilled in the art that the process described hereinbefore refers to a tableting operation conventionally known as molding. In the molding operation, some compression is exerted in the forming of the tablets. However, the amount of compression applied in this kind of operation does not approach the pressure utilized in preparing compressed tablets. Consequently, the molded tablet does not have the density uniformity observed with compressed tablets. Moreover, no lubricant is required in a molded tablet and it is not necessary to employ any disintegrating agents. All of the materials in a molded tablet can be and generally are wholly soluble in water. In some cases binders such as a simple syrup are added to the trituration prior to molding to aid in the adhesion of the saccharide particles in the molding operation.

The preparation of a nitroglycerin tablet containing 0.32 mg. of nitroglycerin is described in Example 1.

EXAMPLE 1

Ten percent nitroglycerin trituration with beta-lactose in an amount of 17.250 Kg. (containing 1.725 Kg. of nitroglycerin) was triturated in a ball mill with 157.4 Kg. of lactose U.S.P. This trituration proceeded for about an hour after which a uniform blending of the ingredients was accomplished.

The resulting approximately 174.65 Kg. of nitroglycerin trituration was divided into four equal sections.

Six liters of purified water and ten liters of alcohol SD 3A were blended and 0.3 liter of simple syrup was added to the alcohol-water solution. Polyvinylpyrrolidone in an amount of approximately 1.76 Kg. was added to the alcohol-water solution and thoroughly dispersed therein. The resulting polyvinylpyrrolidone dispersion was then divided into four equal sections.

Next, one section each of the nitroglycerin triturations and the polyvinylpyrrolidone dispersions were added to a tumbling mixer and blended and from this mix, tablets containing 0.32 mg. nitroglycerin were formed on a conventional Colton tablet molding machine employing a tablet molding plate having cavities designed to make tablets from the above described composition weighing approximately 32 mg. each. The concentration of the nitroglycerin was about 1 percent, the polyvinylpyrrolidone about 1 percent, the beta-lactose about 9 percent, and the lactose about 89 percent of the final dry tablet weight. As each mix was consumed in the molding operation, additional sections of each of the nitroglycerin triturations and the polyvinylpyrrolidone dispersions were blended together in turn and tablets molded therefrom.

The molded tablets were spread on drying trays and the moisture and alcohol removed therefrom by drying overnight at ambient conditions. The resulting dry nitroglycerin tablets were combined in glass jars which held about 5 lbs. of the dry finished tablets. Samples of the nitroglycerin tablets were removed from representative jars and the tablets analyzed individually for their nitroglycerin content. Coefficient of variation percentages were computed from the individual analyses.

Other concentrations of nitroglycerin in molded tablets, namely 0.15, 0.43 and 0.65 mg. each are recognized in the U.S.P. XVIII (1970). Nitroglycerin tablets containing these amounts of the active agent can be prepared in an identical fashion to that described in Example 1 by altering either the quantity of the excipients blended with the nitroglycerin trituration, or the size of the tablet, preferably the former. When the quantity of excipients are varied to provide for tablets weighing about 32 mg. each and containing respectively about 0.15 0.40 and 0.60 mg. of nitroglycerin, the nitroglycerin content will be about 0.5, 1.25 and 2.0 percent respectively. These same tablets will contain about 1 percent polyvinylpyrrolidone, about 4.5, 11.25 and 18 percent beta-lactose and about 94, 86.5 and 79 percent lactose respectively.

What is claimed is:

1. A sublingual pharmaceutical composition consisting essentially of nitroglycerin, polyvinylpyrrolidone and at least one conventional pharmacologically inert, non-toxic, water-soluble sublingual pharmaceutical excipient chemically compatible with nitroglycerin, said sublingual pharmaceutical composition having a stabilized nitroglycerin content as compared to sublinqual pharmaceutical compositions prepared only from nitroglycerin and at least one of said conventional sublingual pharmaceutical excipients, or a combination of said excipients, and wherein nitroglycerin is the sole pharmacologically active agent, and polyvinylpyrrolidone is the sole stabilizer therefor, and wherein the nitroglycerin is admixed with the polyvinylpyrrolidone in a weight ratio of about 10:1 to 1:4.

2. A stabilized pharmaceutical tablet containing nitroglycerin comprising from about 0.5 to about 5 percent of nitroglycerin, from about 0.5 to about 2 percent polyvinylpyrrolidone, and from about 93 to about 99 percent of an excipient or excipients selected from the group consisting of lactose, beta-lactose, milk sugar, fructose, maltose, sucrose, mannitol, and sorbitol.

3. The pharmaceutical tablet of claim 1 wherein said tablet is comprised of about 0.5 percent nitroglycerin, about 1 percent polyvinylpyrrolidone, about 4.5 percent beta-lactose and about 94 percent lactose.

4. The pharmaceutical tablet of claim 1 wherein said tablet is comprised of about 1 percent nitroglycerin, about 1 percent polyvinylpyrrolidone, about 9 percent beta-lactose and about 89 percent lactose.

5. The pharmaceutical tablet of claim 1 wherein said tablet is comprised of about 1.25 percent nitroglycerin, about 1 percent polyvinylpyrrolidone, about 11.25 percent beta-lactose and about 86.5 percent lactose.

6. The pharmaceutical tablet of claim 1 wherein said tablet is comprised of about 2 percent nitroglycerin, and 1 percent polyvinylpyrrolidone, about 18 percent beta-lactose, and about 79 percent lactose.

7. The method of stabilizing a pharmaceutical tablet of nitroglycerin against the migration of nitroglycerin between such tablets when in contact with each other comprising combining an alcohol-water dispersion of polyvinylpyrrolidone with a nitroglycerin tablet trituration comprised of nitroglycerin and an excipient or excipients selected from the group consisting of beta-lactose, lactose, milk sugar, sucrose, fructose, maltose, mannitol and sorbitol prior to the forming of said tablet, said dispersion being combined with said trituration in an amount to provide for a polyvinylpyrrolidone content of from about 0.5 to about 2.0 percent of the final dry tablet weight, and removing the alcohol-water from the tablets after the latter are formed.

8. The method of claim 7 wherein the polyvinylpyrrolidone is dispersed in an approximately 2:1 alcohol-water solution in a ratio of about 1 part polyvinylpyrrolidone to about 10 parts alcohol-water solution.

9. The method of claim 8 wherein the polyvinylpyrrolidone is admixed with the nitroglycerin trituration in an amount that will represent about 1 percent of the final dry weight of the tablets.

* * * * *